(12) United States Patent
Nielsen et al.

(10) Patent No.: US 9,734,302 B2
(45) Date of Patent: Aug. 15, 2017

(54) MEDICAL DELIVERY DEVICE WITH REGIMEN IDENTIFICATION FEATURE

(71) Applicant: Novo Nordisk A/S, Bagsvaerd (DK)

(72) Inventors: Ole C. Nielsen, Hilleroed (DK);
Michael Monrad, Frederiksberg (DK);
Mads Moeller, Hundested (DK); Torkil Filholm, Dyssegaard (DK)

(73) Assignee: Novo Nordisk A/S, Bagsvaerd (DK)

( * ) Notice: Subject to any disclaimer, the term of this patent is extended or adjusted under 35 U.S.C. 154(b) by 361 days.

(21) Appl. No.: 14/394,844

(22) PCT Filed: Apr. 17, 2013

(86) PCT No.: PCT/EP2013/057970
§ 371 (c)(1),
(2) Date: Oct. 16, 2014

(87) PCT Pub. No.: WO2013/156510
PCT Pub. Date: Oct. 24, 2013

(65) Prior Publication Data
US 2015/0066429 A1   Mar. 5, 2015

Related U.S. Application Data

(60) Provisional application No. 61/638,069, filed on Apr. 25, 2012.

(30) Foreign Application Priority Data

Apr. 17, 2012 (EP) .................................... 12164419

(51) Int. Cl.
*G08B 1/00* (2006.01)
*G06F 19/00* (2011.01)
(Continued)

(52) U.S. Cl.
CPC ............ *G06F 19/3456* (2013.01); *A61J 1/00* (2013.01); *A61J 7/0076* (2013.01); *A61J 7/049* (2015.05);
(Continued)

(58) Field of Classification Search
USPC ................. 340/309.16; 702/177; 700/231
See application file for complete search history.

(56) References Cited

U.S. PATENT DOCUMENTS 5,016,172 A * 5/1991 Dessertine ............ G01G 13/28
128/920
5,860,917 A   1/1999 Comanor et al.
(Continued)

FOREIGN PATENT DOCUMENTS

CN   101084036 A   12/2007
JP   2008515505 A   5/2008
(Continued)

*Primary Examiner* — Lam Nguyen
(74) *Attorney, Agent, or Firm* — Wesley Nicolas

(57) ABSTRACT

A drug delivery system comprising a controller adapted to detect when a given user-actuated operation being part of the expelling of an amount of drug is performed, record detected operations as a function of time, and estimate, based on recorded operations, time parameters for the detected operations, thereby providing time parameters for a medical regimen on which the detected operations are assumed to be based upon.

12 Claims, 7 Drawing Sheets

(51) Int. Cl.

| | | |
|---|---|---|
| *A61M 15/00* | (2006.01) | |
| *A61J 7/00* | (2006.01) | |
| *A61M 5/00* | (2006.01) | |
| *A61J 1/00* | (2006.01) | |
| *A61J 7/04* | (2006.01) | |
| *A61M 5/178* | (2006.01) | |
| *A61M 5/315* | (2006.01) | |
| *A61M 5/31* | (2006.01) | |

(52) U.S. Cl.
CPC .............. *A61J 7/0436* (2015.05); *A61M 5/00* (2013.01); *A61M 5/3129* (2013.01); *A61M 15/00* (2013.01); *A61M 15/008* (2014.02); *G06F 19/345* (2013.01); *G06F 19/3462* (2013.01); *G06F 19/3468* (2013.01); *A61J 2200/30* (2013.01); *A61J 2205/50* (2013.01); *A61M 5/178* (2013.01); *A61M 5/31525* (2013.01); *A61M 2005/3125* (2013.01); *A61M 2205/3379* (2013.01); *A61M 2205/3561* (2013.01); *A61M 2205/3592* (2013.01); *A61M 2205/52* (2013.01); *A61M 2205/70* (2013.01)

(56) References Cited

U.S. PATENT DOCUMENTS

| | | | |
|---|---|---|---|
| 6,656,114 | B1 | 12/2003 | Poulsen et al. |
| 7,158,011 | B2* | 1/2007 | Brue ..................... A61J 7/0481 340/309.16 |
| 7,170,823 | B2 | 1/2007 | Fabricius et al. |
| 9,180,245 | B2* | 11/2015 | Bryant ................ A61M 5/1452 |
| 9,483,620 | B2* | 11/2016 | Reimer ............... G06F 19/3468 |
| 9,501,949 | B2 | 11/2016 | Hansen et al. |
| 2007/0220754 | A1 | 9/2007 | Barbaro et al. |
| 2008/0154513 | A1 | 6/2008 | Kovatchev et al. |
| 2008/0306770 | A1 | 12/2008 | Sysko et al. |
| 2009/0036828 | A1 | 2/2009 | Hansen et al. |

FOREIGN PATENT DOCUMENTS

| | | |
|---|---|---|
| WO | 99/35588 A1 | 7/1999 |
| WO | 9943283 A1 | 9/1999 |
| WO | 2006/055813 | 5/2006 |
| WO | 2011124711 A1 | 10/2011 |
| WO | 2012040309 A2 | 3/2012 |

* cited by examiner

MEDICAL DELIVERY DEVICE WITH REGIMEN IDENTIFICATION FEATURE

CROSS-REFERENCE TO RELATED APPLICATIONS

This application is a 35 U.S.C. §371 National Stage application of International Application PCT/EP2013/057970 (published as WO 2013/156510), filed Apr. 17, 2013, which claimed priority of European Patent Application 12164419.9, filed Apr. 17, 2012; this application claims priority under 35 U.S.C. §119 of U.S. Provisional Application 61/638,069; filed Apr. 25, 2012.

The present invention generally relates to electronically controlled systems and devices adapted to store information in the form of time parameters for a medical regimen. More specifically, the invention relates to methods and devices providing and generating such information in an efficient way. In specific embodiments the generated information can be stored and subsequently used to e.g. remind a user of an action to be performed or to provide compliance feedback. In an exemplary embodiment the invention is embodied in a pen-formed drug delivery device, however, the invention may be used in many other types of devices, e.g. medical aerosol inhalers, tablet dispensing devices and blood glucose meters etc.

BACKGROUND OF THE INVENTION

In the disclosure of the present invention reference is mostly made to the treatment of diabetes by injection of insulin, however, this is only an exemplary use of the present invention.

Lack of substantial patient compliance with established dosage intervals has long been recognized as a major problem in treating deceases. Typically in treating a patient, a physician will desire the patient to take a needed drug on a specific schedule. The prescribed (or overthe-counter) medicine is usually obtained from a pharmacist, or the doctor himself, with the actual administration of the drug left to the sole control of the patient. However, even a wellmeaning and conscientious patient may frequently fail to take medication at the desired dosage intervals. This may be true even if the medication is carried at all times with the patient. Potential ill effects of lack of compliance with the desired dosage interval may be further compounded if the patient attempts to compensate for missed dosages by taking an increased dose at a later time. Alternatively, the patient may stop taking the medication altogether. Improper dosage may occur whenever the patient has a marginally impaired memory and may not precisely recall taking the medication or correctly judge how much time has elapsed since medicine was last taken.

Patients with diseases, specifically diabetes, which require regular and systematic self-managed treatment regimens, are thus facing the challenge of remembering when to take their medication. Since such regimens can prescribe daily to weekly medication, which furthermore have to be personalised to accommodate the routines of the patient, e.g. meal times, working hours etc. Often patients develop individual, home-brewed, systems to remind them to take their medication. As substantial non-compliance with a desired medication regimen is a major concern, the above problems have been addressed by a number of compliance aid devices which are adapted to provide an alarm or reminder in case a patient does not comply with a programmed schedule for taking a given dose of medicine.

For example, US 2007/0220754 discloses an electronically controlled pill bottle holder which can be programmed by the user to serve as a reminder when the pill bottle is not removed from the apparatus according to the programmed schedule. U.S. Pat. No. 7,170,823 discloses a medical dispenser in which the alarm functionality has been integrated into the dispenser. In a specific embodiment the dispenser is in the form of a pen device for subcutaneous injections of a drug, e.g. a diabetes drug or growth hormone, the pen comprising a main portion with a drug reservoir and a dosing mechanism as well as a cap portion comprising the electronic means for providing the alarm functionality.

WO 99/43283 discloses a pen device which can be programmed with two reminders by actuating a programming button which has to be operated in order to program the reminders. WO 2011/124711 discloses a pen device in which removal of the cap one or more times sets a corresponding number of timestamps which is then used as basis for generating reminders.

For a more complex regimen the set-up of a drug delivery device may be accomplished straight forward by input means on the device itself, e.g. buttons and a display interface to the user, or on another device which is able to communicate with the injection device by means of e.g. NFC or Bluetooth. Such a device could be a mobile phone or a PC or any other equipment equipped with adequate means to do so. The regimen information could also be embedded in another physical item to either be read by the delivery device by electronically means before use or to be inserted into the delivery device and read electronically during use.

When properly programmed these devices serve well to remind a patient that it is time to take his or her medication (or confirm that a given dose was taken or not taken), however, for many patients it may be an obstacle to properly program the device for which reason this type of compliance aid is unlikely to be put in use despite the fact that it may well be very useful for a given patient when the initial difficulties of programming the device have been overcome. Such difficulty is often related to the ability to understand a complex user interface, when attempting to program a personalised reminder scheme.

As a variation of the above concept WO 2012/040309 discloses a concept in which a treatment regimen may be established in view of the patient medication compliance, i.e. pre-set values are used as a basis for determining a compliance level which subsequently is used to establish a treatment regimen.

Having regard to the above, it is an object of the present invention to provide a system allowing pre-defined event related information to be identified and stored in a convenient way, this allowing for example a reminder programming functionality for an electronically controlled device. It is a further object to provide a user interface and device which can be realized in a simple and cost-effective manner.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, a drug delivery system is provided, the system being adapted to estimate time parameters for a medical regimen comprising one or more administering events at a given time within a given period. The system comprises a controller, a drug reservoir or means for receiving a drug reservoir, drug expelling means for expelling an amount of drug from the reservoir, wherein the expelling of an amount of drug requires at least one user-actuated operation to be performed, and wherein the expelling of an amount of drug represents an administering event. The controller is adapted to detect when a given user-actuated operation being part of the expelling of an amount of drug is performed, record detected operations as a function of time, and estimate, based on recorded operations, regimen time parameters for the detected operations, including the periodicity (e.g. a day or a week), and a time or time window for each operation in the estimated period. In this way time parameters for a medical regimen, i.e. the periodicity and the time for each prescribed event, on which the detected operations are assumed to be based upon can be estimated.

In a shorter wording the invention provides a drug delivery system comprising a controller adapted to detect when a given user-actuated operation being part of the expelling of an amount of drug is performed, record detected operations as a function of time, and estimate, based on recorded operations, time parameters for the detected operations, thereby providing time parameters for a medical regimen on which the detected operations are assumed to be based upon.

As appears, normal use of the system in accordance with a prescribed regimen thus provides automatic programming of the regimen which can then be used for e.g. a reminder scheme or the calculation of a compliance value, this in contrast to known devices and systems which requires specific and additional user-operations to program e.g. reminders.

Indeed, the detected operations may vary in time to such a degree that it is not possible to identify the actual regimen behind the operations, i.e. the user is out of compliance to a high degree. For example, if the regimen tells a patient to take a dose of drug at 20:00 in the evening every day and this then result in the patient taking a dose of drug with a "compliance" of +/−10 hours over a week, then the regimen may be estimated incorrectly as having a periodicity of one week with every recorded action as a prescribed time. To prevent this, the given algorithm estimating the regimen may be designed to detect "unlikely" regimens and indicate an error condition.

The system may be brought into detection mode automatically, e.g. during a given period of time after the system is used for the first time, or it may be left to the user to bring the device into detection mode which may then be left manually or automatically in accordance with the set-up of the device. The system should acquire usage data during a time period long enough to assure the data-set is representative and sufficient for the patient regimen identification. The length of the period may be determined by the user or it may be based on an analysis of the detected data, i.e. the more complex the usage the more difficult it may be for the system to estimate regimen parameters and the longer it may take to acquire sufficient information allowing the system to estimate the parameters with an acceptable precision.

The system may be provided with information on a number of known regimens for patients using the actual type of system and this could be used to ease or secure the correct identification of the patient actual medical regimen. To further ease the complexity of the task to identify the regimen helpful information would be the specific drug loaded in the drug delivery system. This information could be input to the system by the user, e.g. by means of set-up buttons or by use of another device able to communicate with the system, e.g. a mobile phone or a PC and communicated by e.g. NFC or Bluetooth.

Drug information could also be read by the system either from another physical item, e.g. the drug secondary package (e.g. by NFC reading an RFID tag), or a separate item where the information is displayed or embedded or by some information or characteristics of the drug itself or of the primary packaging of the drug, e.g. a coded information on the label of the drug's primary packaging, e.g. the drug container. Other relevant data which could be indicative for the chosen medical regimen could also be supplied to the system besides drug type and the timing of the injections or the sizes of the injections. If the drug is related to insulin treatment supportive data for the system to figure out a patient's medical regimen could e.g. be the patients BG values, especially when used in combination with taken insulin injections.

When the injection device has identified the patient regimen or has a suggestion for the patient regimen it could take this regimen in use immediately for the comparison of the supposed regimen against the actual regimen or it could first ask the patient to confirm that the regimen is identified correct or to adjust it, e.g. to adjust width of time windows. After initial identification of an estimated regimen the controller may leave the learning mode resulting in a set of static time parameters. Alternatively, the regimen identification may be dynamic incorporating the latest events, e.g. using a window of events for the last 10 days.

When the time parameters for the patient's medical regimen has been identified and accepted, the system may be configured to provide reminders to the user based on the estimated time parameters, e.g. an alarm may indicate that it is time to take an amount of drug. The time parameters may also be used to calculate compliance values.

The present invention may be embodied in a number of different devices in which it is relevant to set and provide reminders, e.g. drug delivery devices, medical aerosol inhalers, tablet dispensing devices and blood glucose meters etc. Depending on the type of device and the functionality provided by the device, the kind of user-actuated operation will vary. For example, the operation may be associated with the simple task of "starting" the device, e.g. taking off a cap, flipping a cap or actuating an on-button. Alternatively, the operation may be associated by "real" use of the device, e.g. setting a dose of drug, expelling a dose of drug, or determining a BG value.

In exemplary embodiments the device is a drug delivery or drug dispensing device and the user-actuated operation is related to administration of a dose of a drug. The device may comprise a main portion with a drug reservoir and a drug administration mechanism, a cover portion releasably coupled to the main portion, and contact means arranged to detect when the cover is operated, such that the user-actuated operation is provided by operating the cover and actuating the contact means. The operation may e.g. be between a closed and an open state, between a closed and an open state, or between a locked and an un-locked state. The cover could e.g. be opened by a pivoting or sliding relative movement between the main portion and the cover, or the cover could be fully removable from the main portion. The user-actuated operation could also be the setting or expelling of a dose of drug.

Depending on the type of the device the electronic means for identifying the regimen parameters, setting the reminders and detecting user-actuated operations could be arranged in different parts of the device. For example, for a mechanical device without "inherent" electronic means the electronic means for the reminder functionality could be located in the device per se or in a cover. In the latter way a basically mechanical device could be up-graded with reminder functionality in a simple and cost-effective way. On the other hand, if electronic means is already provided for other reasons, then the regimen identification and reminder functionality may be realized by utilizing these electronic means. For example, some drug injection devices are provided with an electronic display and/or memory, e.g. OptiClik™ from Aventis and HumaPen® Memoir™ from Eli Lilly. Indeed, if the device is adapted to cooperate with a drug container like e.g. a tablet bottle then the electronic means will be located in the bottle receiving device.

As also disclosed above, depending on the type of drug and the corresponding treatment regimen for a given patient the device may be set up to register a specific type of regimen. For example, the programming mode may be active to detect a single user-actuated operation at a given time of the day, whereby a daily reminder could be provided at the detected given time of the day. This kind of functionality would for example be relevant for a diabetes drug which is to be taken once daily, e.g. Levemir® or Victoza® from Novo Nordisk. Alternatively, the programming mode may detect a number of user-actuated operations at given times of the day whereby daily reminders are provided corresponding to the estimated given times of the day. This kind of functionality would for example be relevant for a diabetes drug which is to be taken e.g. 3 times daily in relation to a meal, e.g. NovoRapid® or NovoMix® from Novo Nordisk.

To avoid that the user has to set a clock, the processor may be controlled by a non-real time clock, e.g. the clock may be a 24 hours clock which starts to run when the device is switched on for the first time or whenever the device is brought into programming mode. A given reminder may be muted when the corresponding user-actuated operation is performed within a pre-defined window of time in respect of the given reminder time. For example, if a reminder would sound at 8:00 corresponding to a breakfast meal then actuation of the device between 7:30 and 8:00 would cancel the 8:00 reminder. The reminder may be one of an acoustic, visual or tactile signal or a combination thereof.

To provide a simple and in-expensive device the means for detecting the user-actuated operation may also be used to bring the device into its programming mode. For example, the user may operate the device a number of times within a short period, e.g. the user may take off and put on a pen cap X times within Y seconds. To confirm that the device is now in its programming mode and all previous programming, if any, has been deleted the signal emitter may produce a special signal. In the same way, when the device automatically leaves the programming mode another signal may be used.

The invention also provides a method adapted to estimate time parameters for a medical regimen comprising one or more administering events at a given time within a given period, the method comprising the steps of (i) providing a system comprising a controller, a drug reservoir or means for receiving a drug reservoir, drug expelling means for expelling an amount of drug from the reservoir, wherein the expelling of an amount of drug requires at least one user-actuated operation to be performed, and wherein the expelling of an amount of drug represents an administering event, (ii) detecting when a given user-actuated operation being part of the expelling of an amount of drug is performed, (iii) record detected operations as a function of time, and (iv) estimate, based on recorded operations, regimen time parameters for the detected operations, including the periodicity, and a time or time window for each operation in the estimated period. By this method estimated time parameters for a medical regimen on which the detected operations are assumed to be based upon is provided.

In the context of the present application and as used in the specification and claim, the term controller covers any combination of electronic circuitry suitable for providing the specified functionality, e.g. processing input data and controlling memory as well as all connected or integrated input and output devices. The electronic means may typically comprise one or more CPUs or microprocessors which may be supplemented by additional devices for support or control functions. For example, the sensor and output signal driver may be fully or partly integrated with the processor, or may be provided by individual units. Each of the components making up a processor circuitry may be special purpose or general purpose devices. A sensor for detecting when a user-actuated operation is performed may comprise a "sensor" per se, e.g. in the form of an electrical contact, or an optical or magnetic sensor capable of being influenced by the position of the other unit and adapted to produce a signal which can be recognized and processed by a processor. However, the sensor may also comprise or be associated with circuitry which detects and modifies a signal from a sensor per se before it is sent to the processor. Such circuitry may be formed integrally with a processor.

In a further aspect of the invention an electronically controlled device is provided adapted to store information in respect of scheduled user-actuated operations for a medical regimen, e.g. in the form of estimated data as described above, detect when a user-actuated operation is performed, and for a given time period calculate a compliance value based on the scheduled and the corresponding detected operations, the compliance value being indicative of the user's adherence to the regimen, wherein the compliance value is calculated for a user-selectable time period. In this way compliance values can be provided which are of relevance for different persons, e.g. a shorter 1 week period for patient or a longer 3 months period for a medical practitioner. A number of pre-selected time periods may be stored and subsequently retrieved.

To aid a user's understanding of displayed information the present invention also provides a medical system comprising an electronically controlled display adapted to display a number of different display modes, a value for a type of action, and for a given type of action presenting the value in combination with an associated display mode. The system may be adapted to display a number of symbols, e.g. icons, which can be set to display information in accordance with a number of medical regimens, and be adapted to display a selection of symbols in accordance with a given medical regimen. One or more symbols may be selected in accordance with time of the day for a given action.

As used herein, the term "drug" is meant to encompass any drug-containing medicine in the form of e.g. a liquid, a solution, a gel, a fine suspension, a powder or a gas. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of diabetes related drugs like insulins and GLP-1 like drugs.

BRIEF DESCRIPTION OF THE DRAWINGS

In the following the invention will be further described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not to an actual situation of use. The shown figures are schematic representations for which reason the configuration of the different structures as well as there relative dimensions are intended to serve illustrative purposes only.

Figure 1:
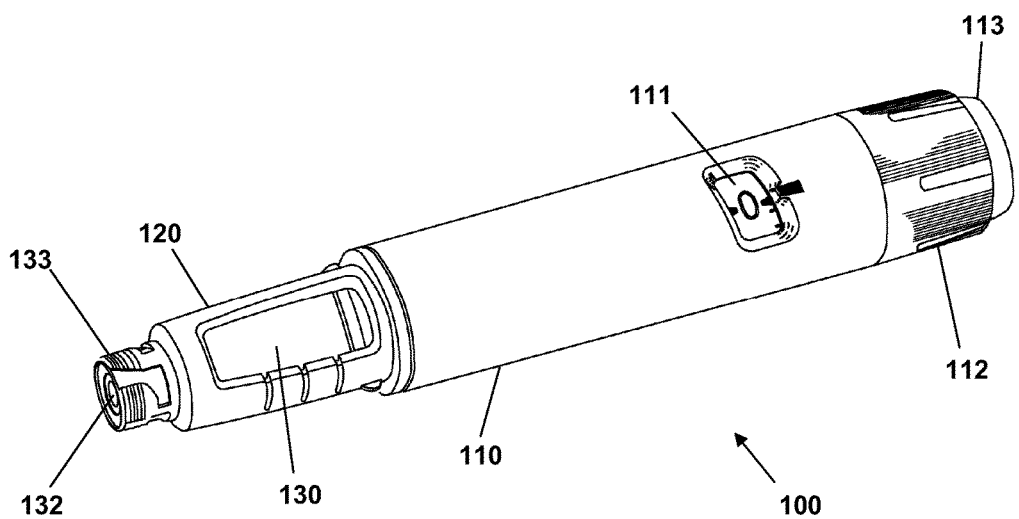
FIG. 1 shows an embodiment of a drug delivery device adapted to be used with a pen cap.

Referring to FIG. 1 a pen-formed drug delivery device 100 will be described. The device represents a "generic" drug delivery device providing an example of a device in combination with which embodiments of the present invention is intended to be used. More specifically, the pen device comprises a cap part (not shown, see FIGS. 6 and 7 below) and a main part having a proximal body portion 110 in which a drug expelling mechanism is arranged or integrated, and a distal cartridge holder portion in which a drug-filled generally transparent cartridge 130 with a distal needle-penetrable septum 132 is arranged and held in place by a cartridge holder 120 attached to the proximal portion, the cartridge holder having openings allowing a portion of the cartridge to be inspected. The device is designed to be loaded by the user with a new cartridge through a distal receiving opening in the cartridge holder, the cartridge being provided with a piston driven by a piston rod forming part of the expelling mechanism. A proximal-most rotatable dose ring member 112 serves to manually set a desired dose of drug shown in display window 111 and which can then be expelled when the release button 113 is actuated. Depending on the type of drug delivery device, the expelling mechanism may comprise a spring which is strained during dose setting and then released to drive the piston rod when the release button is actuated. Alternatively the expelling mechanism may be fully manual in which case the dose ring member and the release button moves proximally during dose setting corresponding to the set dose size, and then moved distally by the user to expel the set dose. The cartridge is provided with distal coupling means in the form of a needle hub mount 133 having, in the shown example, an external thread as well as a bayonet adapted to engage an inner thread or a bayonet of a corresponding hub of a needle assembly (see below). The cartridge holder is adapted to receive and hold the cartridge in a loaded position, the holder having a generally tubular configuration with a distal opening adapted to axially receive the cartridge, the holder and the cartridge being provided with corresponding coupling means allowing a cartridge to be mounted and subsequently released. Different embodiments of such coupling means will be described in greater detail in the following. An example of an expelling mechanism allowing a user to set a desired dose as well as comprising a cartridge actuated coupling allowing the piston rod to be pushed back by a cartridge during loading is disclosed in e.g. US 2004/0210199 hereby incorporated by reference. A further example of a pen-formed drug delivery device is known from WO 99/38554 to which reference is made for further details in respect of the internal construction of the shown type of pen.

When using a drug delivery device of the above general type (which may have other formfactors and also be provided with a motorized expelling mechanism), the user is typically recommended to take a subcutaneous injection by performing the following steps: remove the cap to uncover the needle mount, mount a new needle assembly, set a dose amount to be expelled by rotating the dose setting member, when the needle has been inserted subcutaneously actuate the release means for driving or releasing the drug expelling means to expel the set dose, after having withdrawn the needle from the skin remove the needle assembly from the needle mount, and re-attach the cap to cover the needle mount.

The purpose of the disclosed drug delivery device is to provide an easy-to-use reminder programming functionality, where normal use of the drug delivery device provides automatic programming of a reminder scheme based in estimated time parameter values for a drug regimen as e.g. prescribed by a patient's medical practitioner. The device may be intended to be used with a single type of drug, e.g. a diabetes drug which is to be taken once daily, e.g. Levemir® or Victoza® from Novo Nordisk, or a diabetes drug which has to be taken twice or more daily, e.g. NovoRapid® or NovoMix® from Novo Nordisk, or it may be a general-purpose device adapted to identify a variety of drug regimens. In the following a number of examples illustrating different aspects of the present invention will be given.

Tables 1a, 1b, 1c and 1d show examples of medical regimens identified as a result of an analysis performed by the injection device on a number of previously taken injections. It contains a number of data set containing injection time and injection amount information with a repetition period, i.e. a 'wrap around' time.

TABLE 1a

[6 h 30 m, 7 h 30 m] & [30, 35] IU

Table 1a shows a once daily regimen, systematic with a 'wrap around' time of 24 hours. Each day the patient is supposed to make an injection between half past 6 and half past 7 in the morning (i.e. 6.30, 7.30) and with an out-dosing amount between 30 and 35 IU (International Units).

TABLE 1b

[6 h 30 m, 7 h 30 m] & [30, 35] IU
[18 h 30 m, 19 h 30 m] & [30, 35] IU

Table 1b shows a twice daily regimen, systematic with a 'wrap around' time of 24 hours. Each day the patient is supposed to make an injection between half past 6 and half past 7 in the morning (i.e. 6.30, 7.30) and again in the evening between half past 6 and half past 7 o'clock (i.e. 18.30, 19.30). Both in the morning and in the evening the out-dosing drug amount should be between 30 and 35 IU (International Unit).

TABLE 1c

[1 d 6 h 30 m, 1 d 7 h 30 m] & [30, 35] IU
[1 d 18 h 30 m, 1 d 19 h 30 m] & [30, 35] IU
[2 d 6 h 30 m, 2 d 7 h 30 m] & [30, 35] IU
[2 d 18 h 30 m, 2 d 19 h 30 m] & [30, 35] IU
[3 d 6 h 30 m, 3 d 7 h 30 m] & [30, 35] IU
[3 d 18 h 30 m, 3 d 19 h 30 m] & [30, 35] IU
[4 d 6 h 30 m, 4 d 7 h 30 m] & [30, 35] IU
[4 d 18 h 30 m, 4 d 19 h 30 m] & [30, 35] IU
[5 d 6 h 30 m, 5 d 7 h 30 m] & [30, 35] IU
[5 d 18 h 30 m, 5 d 19 h 30 m] & [30, 35] IU
[6 d 6 h 30 m, 6 d 7 h 30 m] & [30, 35] IU
[6 d 18 h 30 m, 6 d 19 h 30 m] & [35, 40] IU
[7 d 8 h 00 m, 7 d 9 h 00 m] & [35, 40] IU
[7 d 20 h 00 m, 7 d 21 h 00 m] & [30, 35] IU

Table 4c shows a twice daily regimen, systematic with a 'wrap around' time of 7 days. It can be seen that the first 5 days the regimen is the same each day but for the last 2 days (day 6 and 7) the out-dosing time and amount differs a little.

TABLE 1d

[7 h 30 m, 8 h 30 m] & [20, 35] IU
[12 h 30 m, 13 h 30 m] & [30, 35] IU
[18 h 30 m, 19 h 30 m] & [40, 45] IU

Table 1d, shows a three times daily regimen, systematic with a 'wrap around' time of 24 hours: Injections taken in a time window morning, midday and evening and with three different out-dosing intervals.

Figure 2:
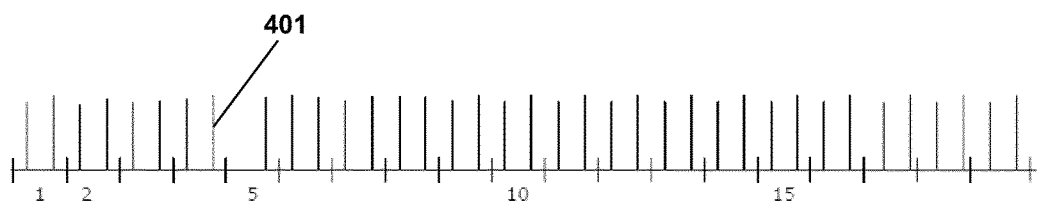
FIG. 2 shows drug-dosing related events as a function of time.

As mentioned above the identification of the patient regimen can be performed in different ways by using automatic analytical methods conducted by the injection device. The most general regimen analytical algorithm is where the injection device figures out which regimen the patient is following by solely acquiring patient usage date during a time period. When doing this it has to arrange the data in a systematic way to identify the regimen. A very important variable in doing this is the above mentioned time 'wrap around' defining the systematic time period for the treatment. For example, if the medical regimen or treatment is dividable into a time period of one day, e.g. once or twice daily treatment, this is the systematic 'wrap around' time period. FIG. 2 shows the event timing 401 for a twice daily treatment, e.g. with a basal insulin, where the patient has taken the insulin almost all the days but forgot one injection one day. The medical regimen analysing program will go through a number of different possibilities for the systematic time period, e.g. beginning with a single day to see if the acquired data set can be fit into this, if not then use a 2 day period and so on with longer and longer time periods. Some systematic time periods can also be preselected as being more probable than others, e.g. one day, two days, one week or two weeks.

As an example an overall method could be (i) identify the time 'wrap around' period, (ii) identify the regimen number of out-dosing per time period, and (iii) eventually compare and further fit more closely the found regimen with one of a number of preselected regimen.

Figure 3:
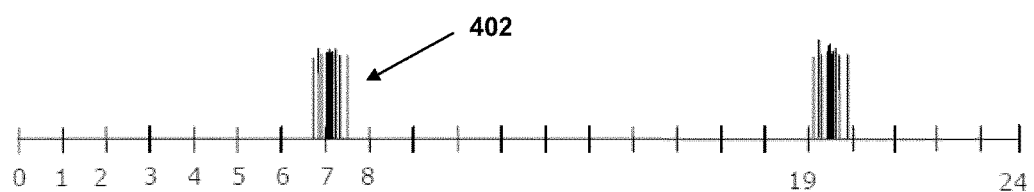
FIG. 3 shows drug-dosing related events as a function of time grouped together.

In FIG. 3 it is shown how the data set fits into a one day period example in general. It can also be seen that the algorithm is implemented to separate different collections of data set within this systematic time period of one day. This separation method can be based on advanced or simple statistical methods including just a simple algorithm able to count the number of observations within small time slots over the entire day and to identify by comparison if there are one, two or more groups of data set. The belonging of data set between 2 or more groups 402 within the same 'wrap around' time can be identified by calculations of mean values and standard deviations of the two or more groups to see where a belonging of a data set gives the overall less standard deviations for all the groups of data set. Other possibilities for reducing the impact in the estimated medical regimen from erroneous injections (outliers) could be using median value instead of, or complementary to mean value, and/or to filter the data set by extracting and using data sets only below a certain percentile, e.g. 85%. The 'wrap around' time in this example day is to be regarded as a time period of a certain length but not necessary bound to an actual day fitting into a calendar, i.e. the time period day could overlap 2 consecutive calendar days (and equivalently with other 'wrap around' time periods of several days or weeks). In FIG. 3 the algorithm has identified two groups 402 of data sets each day (here for simplicity shown within a calendar day). The total collection of acquired data set can be extended into a long time period of many days to assure the data set is large enough to be representative for the estimated time distribution of the injections. This time period can be limited to only include a certain number of historic data to let the regimen estimator be adaptable to changes in patient behaviour or usage of the device or to let the regimen estimator be able to adapt to changes in time zones, daylight savings time, changes in regimen or other deviations from the regimen including changes in patient behaviour. This time window can be linearly weighted (e.g. moving window) or weighted in a way that the weighting of the data set is dependent of how old or new they are, e.g. newest data set has the highest importance (e.g. exponential weighing).

Figure 4A:
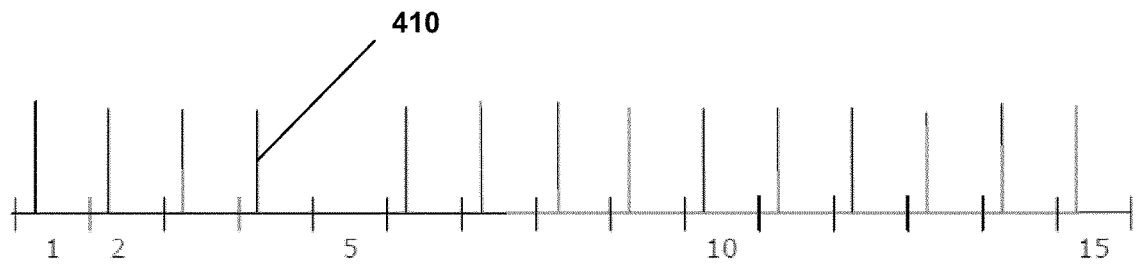
FIG. 4A shows drug-dosing related events as a function of time.
Figure 4B:
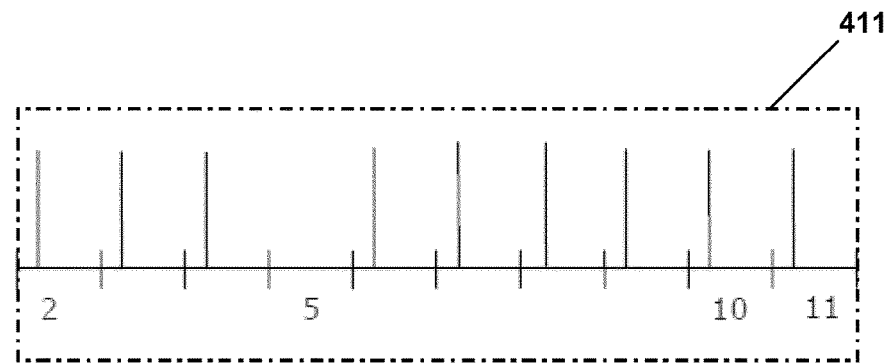
FIGS. 4B and 4C show drug-dosing related events seen through a time window.
Figure 4C:
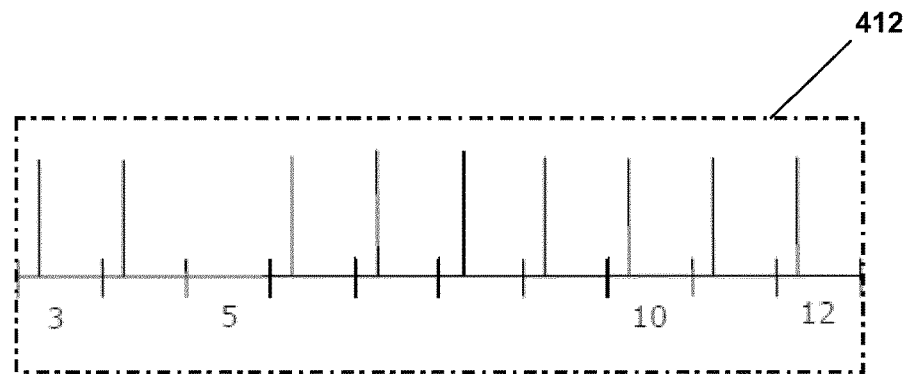

FIGS. 4A, 4B and 4C show data from a once daily regimen with a linear moving window filter where only data set from a certain time period is included into the regimen estimator, here 10 days. FIG. 4A shows the data sets 410 for 15 days, and FIGS. 4B and 4C show the data sets after the linear moving window filter 411, 412 has extracted the wanted data set for 10 days period for two consecutive days: day 2-11 and 3-12. No dose was taken on day 5.

If an out-dosing (injection) regimen change is big, as would normally be the case in changes in time zones, the regimen estimator cannot necessary cope with the change in a transparent way for the user for which reason the device may warn or alert the user correspondingly for a period of time. However, after some time the estimator will include the regimen alterations into the new estimate automatically. Another way to cope with big alterations in regimen is to include the patient into some kind of set-up decision or decision to postpone the delivery device's warnings/alerts until the estimator is updated.

It is common to precede an injection with an air shot or otherwise priming of the device. This to assure that the device is working properly or to remove air or air bubbles in the liquid system or to align/attach the injection devices piston rod with the drug containers piston. If the device is able to sense the dismantling of the cap from the device, e.g. if the electronics of the device is located in the cap, then this would not provide a problem as normally the user will not put the cap back on between the two operations. However, if other inputs are detected, e.g. expelling of a dose, the regimen estimator algorithm may recognize such an event. For example, if the time between two expelling actions is within a short period of time, e.g. 1 minute, the two actions may be recognized as a single dosing event. Such an algorithm could also take into account the amount of out-dosing in order to differentiate between a divided out-dosing and a preceding air shot/priming out-dosing.

With reference to FIGS. 4A-4C an embodiment of a regimen estimator will be described. The data set is distributed relative to day time for a moving window period 411, 412 of many days, in this embodiment set to 10 days. The regimen estimator calculates the mean value of injection day time, the standard deviation and calculates a confidence interval, e.g. 95% and presuming normal distribution, to calculate the time window boundaries within which the next injection has to take place if the medical regimen is followed based on the historic data from the 10 previous days and the chosen confidence interval.

When identifying and using a confidence interval, this could be combined with always assuring that it is within a certain interval and if outside then reduced to a certain maximum or increased to a certain minimum value. This to prevent that a patient who adopts to the regimen estimators analysed interval will be led to a still narrower interval or on the other hand a patient who always a number of times are outside the interval could be led to a still bigger interval.

TABLE 2

Data sets corresponding to the data sets in FIG. 4B, i.e. from a moving window of days 2-11 (10 days), where the injection has been forgotten one day. The table contains both injection time as well as injection a mount data.

| Day | Time | amount |
| --- | --- | --- |
| 2 | 6 h 02 m | 40 IU |
| 3 | 6 h 05 m | 41 IU |
| 4 | 6 h 00 m | 40 IU |
| 5 | | |
| 6 | 6 h 12 m | 40 IU |
| 7 | 6 h 38 m | 45 IU |
| 8 | 6 h 41 m | 45 IU |
| 9 | 6 h 11 m | 40 IU |
| 10 | 6 h 08 m | 39 IU |
| 11 | 6 h 10 m | 40 IU |

TABLE 3

Data sets corresponding to the data sets in FIG. 4C, i.e. for days 3-12 (10 days).

| Day | Time | Amount |
| --- | --- | --- |
| 3 | 6 h 05 m | 41 IU |
| 4 | 6 h 00 m | 40 IU |
| 5 | | |
| 6 | 6 h 12 m | 40 IU |
| 7 | 6 h 38 m | 45 IU |
| 8 | 6 h 41 m | 45 IU |

TABLE 3-continued

Data sets corresponding to the data sets in FIG. 4C, i.e. for days 3-12 (10 days).

| Day | Time | Amount |
| --- | --- | --- |
| 9 | 6 h 11 m | 40 IU |
| 10 | 6 h 08 m | 39 IU |
| 11 | 6 h 10 m | 40 IU |
| 12 | 6 h 11 m | 40 IU |

Based on data in tables 2 and 3 the mean day time value and the approximate 95% confidence interval can then be calculated.

Mean day time value to be used for day 12 respectively day 13:

$$t_{mean,2,11} = \frac{1}{n}\sum_{2}^{11} t_i \ \& \ t_{mean,3,12} = \frac{1}{n}\sum_{3}^{12} t_i,$$

'n' being the actual number of data sets in the data window (excluding day 5).

The (approximately) 95% confidence interval window:

$$[t_{mean}-2*\sigma; t_{mean}+2*\sigma],$$

The numbers for $t_{mean}$ and $\sigma$ is from the moving actual window of data set (day 2-11 or day 3-12).

The calculated statistical population standard deviation s is used for $\sigma$, i.e.

$$\sigma = s = \frac{1}{n}\sqrt{\sum_{a}^{b}(t_i - t_{mean})^2},$$

'n' being the actual number of data set in the data window, 'a' is the first day and 'b' is the last day in the moving window of data set (2, 11 respectively 3, 12 in the examples).

The actual calculation of confidence interval to be used to compare the next injection time which can be set more or less aggressively. For example, a smaller confidence interval will require the next injection to be closer to the mean value than a wider interval.

Though the calculation shown here is simple much more advanced calculations can be taken into account including fitting against special distributions, dynamic length windows (number of samplings of data set) e.g. requiring certain values for the statistical variance. These statistical variance targets could also be depending of the result itself for an estimated regimen.

For table 2 the mean day time for injection can now be calculated by:

$$t_{mean,2,11} = \frac{1}{n}\sum_{2}^{11} t_i,$$

giving $t_{mean,2,11}$=6h13m

And the (approx.) 95% confidence interval for injections day time can be calculated by:

$$[t_{mean} - 2*\sigma_t; t_{mean} + 2*\sigma_t],$$

with $$\sigma_t = s_t = \frac{1}{n}\sqrt{\sum_{a}^{b}(t_i - t_{mean})^2}$$

Giving 95% confidence interval=[5h45m, 6h41m] (day 5 not included in the calculation).

The regimen in this embodiment is a once daily injection taken between 15 minutes to 6 o'clock and 19 minutes to 7 o'clock for day 12. It can be seen that the delivery time for day 12 is within the confidence interval calculated above [5h45m, 6h41m], namely at 11 minutes past 6 o'clock. Correspondingly, the delivery at day 12 is regarded done accordingly to the patient's medical regimen as defined by the regimen estimator of the injection device.

With regard to the data set of table 3 the regimen estimator now estimates a new confidence window for the injection time, this is [5h48m, 6h42m] to be used for day 13.

A more sophisticated regimen estimator can also include the amount of insulin taken each time. Indeed, this would require a drug delivery system with dose capture and not just a relatively simple cap device. For example, to fit both for injection time and out-dosing amount in the 'wrap around' time period. If the injection times fit but not the belonging out-dosing amount, it can be caused by the 'wrap around' time is to short, e.g. day based and not week based thereby not including patient's weekend/workday differences in behaviour or it could be caused by the medical regimen requires different drug amount at different times of day or caused by different actual needs during the day or week. The estimator tries to use as short a period ('wrap around' time) as possible taking both time and out-dosing amount into account. If it is not able to fit within required margins (e.g. measured in standard deviations) it should extend the period to a next level and make a new calculation on the acquired data set and data set groups. If still not able to fit it should extend to the next following level and so on.

If after a certain time (this time either set up in the device initially or by a user or possibly derived from the acquired data set itself) the regimen estimator still can't find a fit for both the time of injection regimen as well as the belonging injections amount it can either choose to only use the time information for the regimen or ask the user to suggest a regimen or to continue the acquiring of data set trying to get a fit.

If the regimen estimator identifies the medical regimen including a number of out-dosing then also the expected amount belonging to the out-dosing time can be estimated in similar ways as the injection time itself by using more or less sophisticated statistical methods. A simple estimate (for the next out-dosing amount) can be based on a confidence interval similar to the one described above for the time of out-dosing.

E.g. by using data set from the table in table 2, the mean out-dosing amount is:

$$v_{mean,2,11} = \frac{1}{n}\sum_{2}^{11} v_i$$

And the (approx.) 95% confidence interval for out-dosing amount can be calculated by:

$$[v_{mean} - 2*\sigma_v; v_{mean} + 2*\sigma_v],$$

with $$\sigma_v = s_v = \frac{1}{n}\sqrt{\sum_{a}^{b}(v_i - v_{mean})^2}$$

And with the actual values inserted the (approx.) 95% confidence interval for the out-dosing amount based on day 2 to 11 is calculated to [37, 45] IU.

When out-dosing (or not) on day 12 the out-dosing time and amount can be compared with the time window and amount window based on the above calculated 95% confidence intervals based on data set from day 2 to day 11.

As can be seen in the example above based on table 2 the 95% confidence interval is [5h45m, 6h41m]. This means that according to the regimen estimator the next delivery should take place between 5:45 and 6:41. Besides deliveries being within this time window also the amount of out-dosed drug can be compared with the calculated estimate. As can be seen from the example above the (approx.) 95% confidence interval is [37, 45] IU. So with this regimen estimator the next out-dosing amount should be within this window. There are three different cases when comparing a given dose delivery with the calculated time interval.

A: If an Injection is Taken Before the Time Window

Figure 5A:
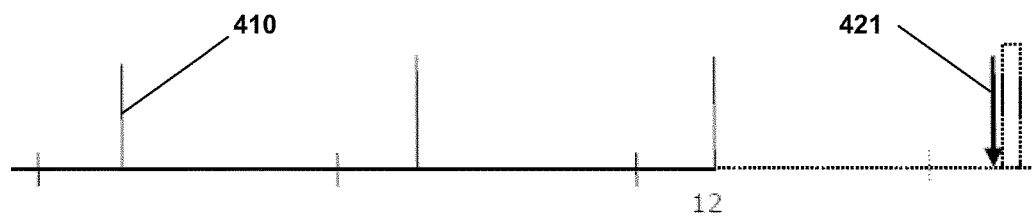
FIGS. 5A, 5B, 5C, and 5D show different situations of an event taking place relative to an estimated time window for that event.
Figure 5B:
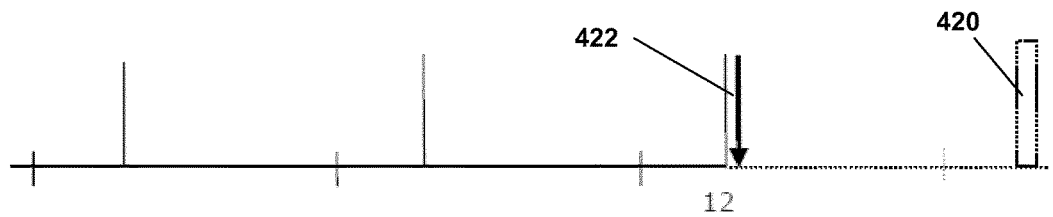

FIG. 5A shows the 3 last out-dosing events 410 in the moving window example of FIG. 4C. The last event is numbered 12. The regimen estimator calculates the out-dosing confidence level for time of out-dosing indicated in FIG. 5A by the rectangle 420. The bold arrow 421 indicates an event indicative of an out-dosing taking place before the dashed time window from the regimen estimator, which may cause a more or less distinct warning (or alert) to the patient. For example, if an event 422 takes place much earlier as shown in FIG. 5B it could represent a double injection which may result in a strong warning. Depending on what kind of event is detected by the system, the assumed attempt to deliver a double dose could be treated in different ways. For example, if the system electronics detects a cap-off event then putting back the cap within e.g. 30 seconds could cancel the event. If the system electronics is integrated in the delivery device dose setting mechanism and the user starts to set a dose, then simply dialing back the dose to zero would cancel the event. If expelled dose sizes are detected then a split dose in which a dose is taken by 2 injections within a short time can be detected and counted as a single event.

B: If an Injection is Taken within the Time Window

Figure 5C:
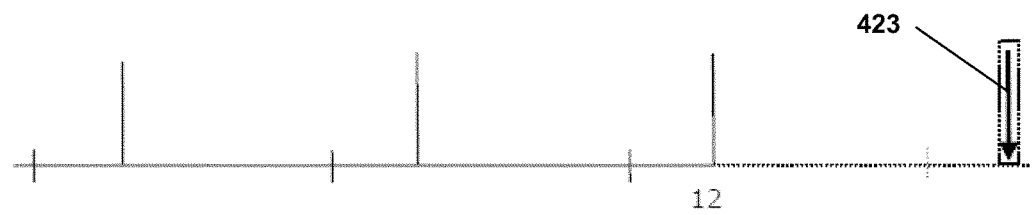

FIG. 5C shows a situation where the out-dosing event 423 is performed within the estimated regimen window.

C: If an Injection is Taken after the Time Window

Figure 5D:
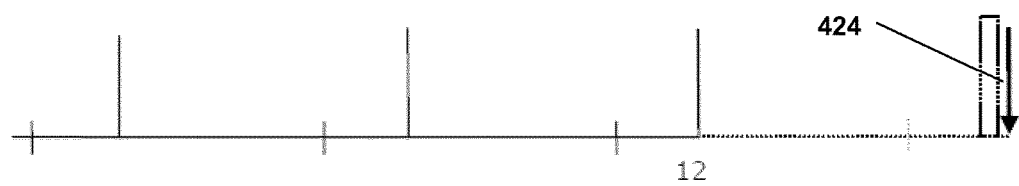

FIG. 5D shows a situation where the out-dosing event 424 is performed after the regimen time window for the next out-dosing. Also here a warning can be communicated to the patient.

If the drug delivery system is adapted to detect the amount of expelled drug, warnings may be given if doses outside the estimated range for an estimated dose-delivery may be given. The means of communication may include any suitable means for making a visual, audible or tactile signal. Besides communicating directly to the patient the information can also be sent to other devices, e.g. a person's smartphone or computer network by electronics means including NFC and RF communication.

Figure 6:
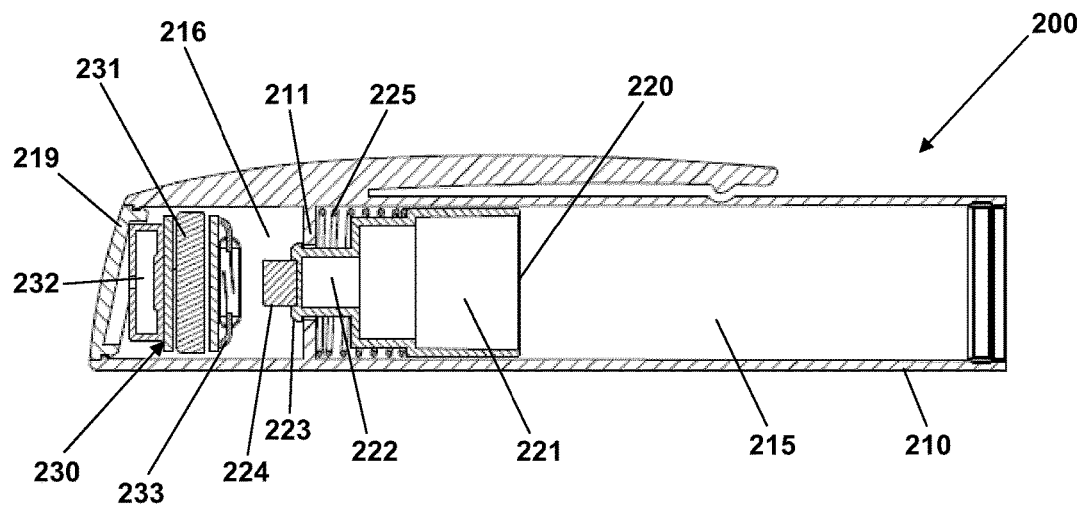
FIG. 6 shows a first embodiment of a pen cap comprising electronic means.
Figure 7:
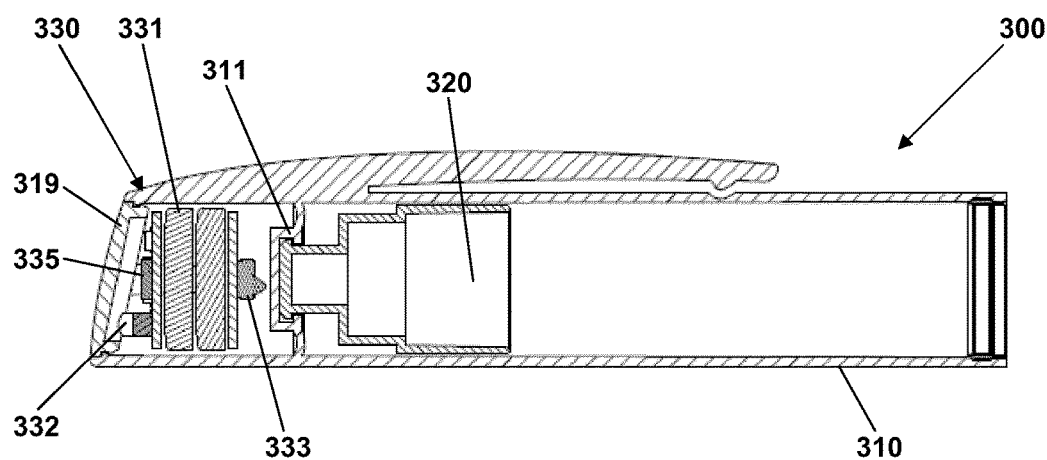
FIG. 7 shows a second embodiment of a pen cap comprising electronic means.

With reference to FIGS. 6 and 7 schematic representations of cap devices adapted to be used with the pen-formed drug delivery device of FIG. 1 will be described, such cap devices providing a platform for a specific implementation of the present invention.

FIG. 6 shows a pen cap 200 adapted to be used with a pen body having a general design as the pen body 110 shown in FIG. 1. The pen cap 200 comprises a housing 210 with an inner partition wall 211 dividing the interior of the cap in a proximal cavity 215 adapted to receive a distal portion of a pen body with a mounted needle assembly, and a distal cavity 216 closed with a distal lid member 219, the wall having a central opening adapted to receive and hold an actuation member 220. The actuation member comprises a proximal skirt portion 221 adapted to receive and engage a needle assembly, and a distal cylindrical portion 222 adapted to be received in sliding engagement in the central opening of the wall partition, the cylindrical portion being provided with a distal circumferential flange 223 adapted for locking engagement with the central opening as well as a small magnet 224. Between the partition wall and the skirt portion a spring 225 is arranged to bias the actuation member in a proximal direction. The skirt portion and/or the cylindrical portion are adapted to provide a seal between the two cavities, this preventing e.g. fluid from entering the distal cavity.

In the distal cavity the electronic means 230 providing the reminder functionality of the cap is arranged, the electronic means comprising a processor and associated memory (not shown), an electric cell 231 ("battery"), a buzzer 232 and a read switch 233 which is actuated when the actuation member is moved distally when a pen body is inserted in the proximal cavity of the pen cap. Depending on the specific design of the actuation member, actuation of the read switch may or may not require that a needle assembly is mounted on the pen body.

FIG. 7 shows a pen cap 300 having the same general design as pen cap 200 described above, however, the actuation member 320 is fixedly locked to a flexible partition wall 311 which both allows axial travel of the actuation member and provides a proximal-directed spring force on the actuation member. The flexible partition wall may be formed integrally with the pen cap housing 310 as shown, or may be a separate member mounted in the housing. The electronic means 330 comprises a processor 335 and associated memory, two electric cells 331, a LED 332 and a mechanical switch 333 which is actuated when the actuation member 320 is moved distally. The distal lid member 319 is transparent allowing a user to observe the LED. The electronic means may also be provided with communication means, e.g. an IR LED or a radio transmitter, allowing communication between the pen cap electronics and an external system, e.g. a PC at the doctor's office.

In the shown embodiment of FIG. 1 the drug delivery device is a pre-filled pen device intended for single use only, however, the pen could also be a durable device intended to be used with exchangeable drug cartridges. In case the pen is of the durable type it may be provided with electronic means for detecting and creating a dose log which then could be transmitted to the cap device of FIG. 6 or 7.

Figure 8:
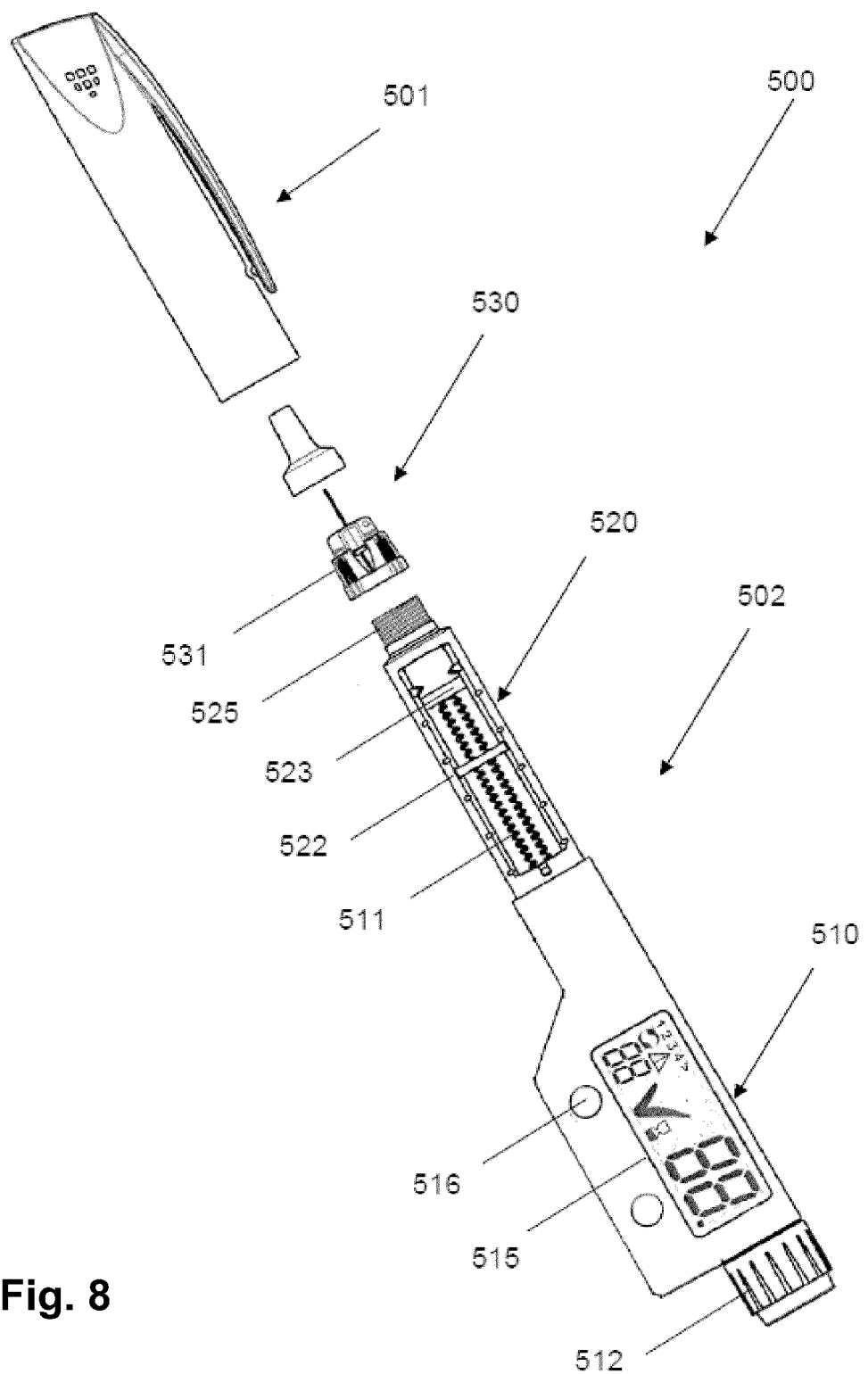
FIG. 8 shows a drug delivery device comprising electronic logging and display means.

FIG. 8 shows such a pen 500. The pen device comprises a cap portion 501 (here shown as a normal cap not related to the above-described cap devices 200, 300) and a main portion 502 having a proximal part 510 in which a drug expelling mechanism is arranged, and a distal reservoir part 520 in which a replaceable drug-filled transparent cartridge with a distal needle-penetrable septum is arranged and hold in place by a cartridge holder 522 releasably mounted to the proximal part, the cartridge holder having openings allowing a portion of the cartridge to be inspected. The cartridge is provided with a piston 523 driven by a piston rod 511 forming part of the expelling mechanism, the piston rod being adapted to be pushed back when a new cartridge is mounted. A proximal-most button 512 serves to manually set and expel a desired dose of drug. This type of a mechanical pen-formed drug delivery device is well known, see e.g. WO 99/38554 to which reference is made for further details in respect of the internal construction of the shown type of pen. The cartridge (or alternatively the cartridge holder) is provided with distal coupling means in the form of a hub mount 525 having, in the shown example, an external thread adapted to engage an inner thread of a hub 531 of a needle assembly 530. The proximal part further comprises a display 515, user actuatable keys 516 as well as electronic means (not shown) for detecting and storing information representing operations performed by the expelling mechanism. The detection means for detecting a set and/or expelled dose may be adapted to detect directly or indirectly the position of the piston rod, see e.g. U.S. Pat. No. 6,585,698 which is hereby incorporated by reference. In the shown embodiment the electronic means is adapted to store data representing injections performed by the user in the form of a time and dose log. The display may show the actual dose being set by a user using the button 512, the last dose (e.g. amounts of units expelled) and the time since last dose (or the actual time for the last dose), or the user may use the keys 516 to scroll through the log to display previous expelling data. The pen is adapted to transmit data to another system or device, which in the present context would be the cap devices of FIGS. 6 and 7.

Figure 9:
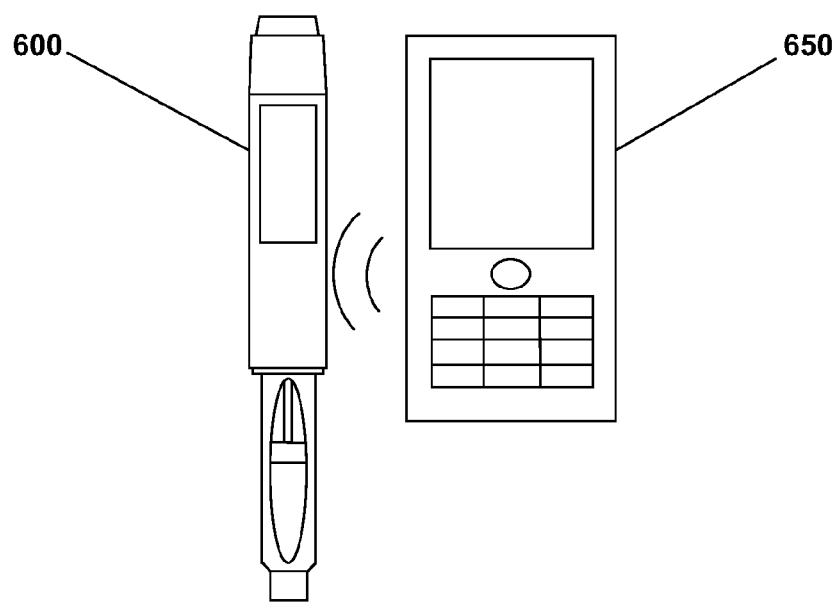
FIG. 9 shows a drug delivery device in combination with a smartphone.

If the device already contains information on a number of known regimens for patients using the actual type of injection device this could be used to ease or secure the correct identification of the patient actual medical regimen. Correspondingly, the pen may be adapted to receive data to be used by the estimating algorithm. For example, to ease the complexity of the task to identify the regimen helpful information would be the specific drug loaded in the injection device. This information can be input to the injection device by the user, e.g. by set-up buttons on the device or by use of another device able to communicate to the device, e.g. a mobile phone or a PC and communicated by some communication protocol, e.g. NFC or Bluetooth. FIG. 9 shows an example of such a system comprising a pen device 600 with electronic means in combination with an NFC enabled smartphone 650.

Figure 10:
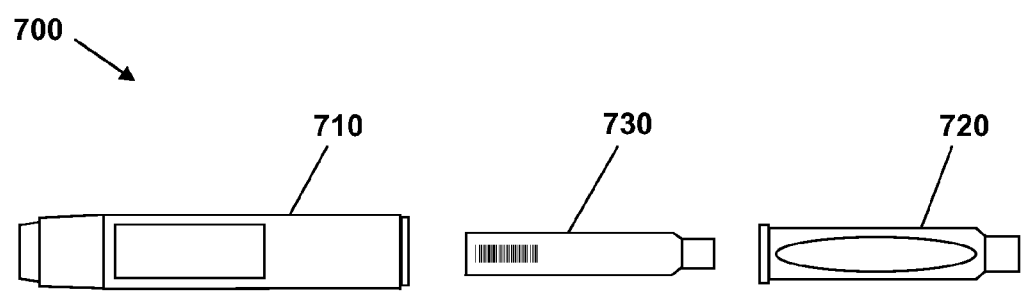
FIG. 10 shows a drug delivery device adapted to receive and read information from a coded cartridge.

The drug information could also be read by the injection device either from another physical item, e.g. the drug secondary package (e.g. by NFC reading an RFID tag), or a separate item where the information is displayed or embedded or by some information or characteristics of the drug itself or of the primary packaging of the drug, e.g. a coded information on the label on a drug container. FIG. 10 shows an example of such a system comprising a pen device with a body part 610 comprising electronic means, and a distal cartridge holder 620 in which a replaceable bar-coded drug-filled transparent cartridge can be received and hold in place. Also other relevant data which could be indicative for the chosen medical regimen could be entered into the injection device's regimen analyser besides drug type and the timing of the injections or the sizes of the injections. If the drug is related to insulin treatment a supportive data for the device to figure out the patient's medical regimen could e.g. be the patients BGM values, especially when analysed in combination with taken insulin injections.

When a drug delivery system has been provided with information in respect of a medical regimen to be followed, e.g. by automatic estimation as described above, and is adapted to detect an event indicative of the actions of the regimen being performed, then it would be possible to compare actual events with planned or estimated events, and then calculate a compliance value for a given period. Thus, each event may be evaluated against a criterion which consists of a reference time period termed a "compliance window". The periods before and after the window may either be identical or individually defined, depending on medical considerations. An event inside the compliance window is considered compliant, while an event outside the compliance window is considered none-compliant. The compliance value may be calculated for one or more periods serving different purposes. For example, for the patient it may be of greatest interest to know the compliance for the most recent past, e.g. for the last week, whereas for a medical practitioner a longer period may be relevant, e.g. for a diabetes patient 3 months corresponding to the period for which a $HbA1_c$ measurement is indicative of the patient's average blood sugar concentration.

Calculations of actual use of the device against medical regimen can be performed by utilizing simple statistics or more complex statistics. An example of a simple routine or calculation is to count the number of non-compliant injections against total number of injections for a prolonged period and displaying this calculation as a percentage rate, e.g. a regimen for a 91 day period has resulted in 7 non-compliant situations, e.g. forgotten injection (out-dosing), resulting in a non-compliant percentage of 7/91=7.7%

An example of a slightly more sophisticated calculation could be to count and sum up the amount of out-dosed drug within a period and to compare it with the regimen prescribed or estimated amount together with a count of missed time windows and/or amount windows out-dosed in the period. For example, if for a twice daily regimen for a 7 days period two injections have been forgotten and one injection has been less than the prescribed dose (15 instead of 20 IU), this would result in a non-compliance of total amount of −16% ((235−280)/280), time window −14% (−2/14), amount window −21% (−3/14). More statistical methods can be taken into action e.g. calculations of standard deviation to indicate the spread in deviations.

A further analysis and/or break-down of non-compliance situations to see if there are certain times or certain conditions where it is more likely for the patient to have a non-compliance situation can be identified and displayed. An example could be to break down a prolonged period into e.g. week-days to see if there are certain days and/or time of day where non-compliant situations are more frequent than others. Hereby the patient as well as the caring personal has a fast and efficient method to identify not only compliance or non-compliance of the patient regarding a medical regimen but also to identify potential situations or times where the likelihood for non-compliant behaviour is higher than else.

Figure 11:
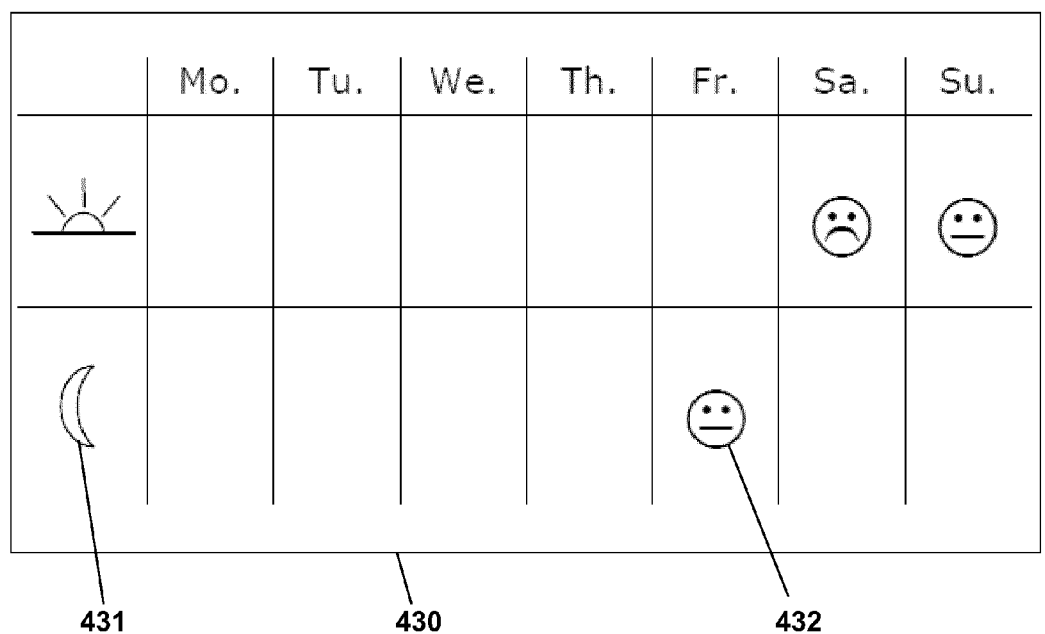
FIG. 11 shows a display configured to show compliance indicators for an identified regimen.

An example of this is shown in FIG. 11 depicting a display 430 on e.g. a drug delivery device or on a smartphone to which data from a drug delivery device has been transmitted. Here a twice daily regimen (morning and evening, symbolized by a morning rising sun and a moon 431) is broken down into a week pattern for a prolonged period of several weeks and shows by 'smileys' 432 that a non-compliant issue exists for Friday evening, Saturday morning and Sunday morning. This could be a sum-up of the drug amount out-dosed for the 14 fields in the 2×7 matrix table and compared against expected out-dosings for the medical regimen. The results are compared and a decision based on the agreement and size of disagreement results in an assessment in 'good' compliance, 'less good' compliance and 'poor' compliance. The smileys for Friday and Sunday are showing a 'less good' compliance and for Saturday a 'poor' compliance. The 'happy' smileys (representing 'good' compliance) for the rest of the times are for clarity not showed. The criteria for assessments of non-compliant behaviour can be made fixed, relative or even dynamically adaptable to the medication, the medication doses, the medication timing and/or the patient's degree of compliant behaviour.

As the regimen will differ from patient to patient the system is configured to generate a display view adapted to the identified regimen. As appears, the FIG. 9 display has been configured to show a twice daily regimen for a week period. In addition to the general 2×7 display format the system is configured to generate icons which will aid the patient in reading and understanding the displayed information, i.e. in the shown example events recognised as morning events are characterized with a rising 'morning sun' icon just as evening events are characterized with a 'moon' icon. The smileys are selected according the degree of compliance.

In the above a pen-formed drug delivery device is used to illustrate different examples embodying aspects of the present invention, however, the invention may be used in many other types of devices, e.g. medical aerosol inhalers, tablet dispensing devices and blood glucose meters etc.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery system adapted to estimate time parameters for a medical regimen comprising one or more administering events at a given time within a given period, comprising:
   a controller,
   a drug reservoir or structure for receiving a drug reservoir,
   drug expelling structure for expelling an amount of drug from the reservoir,
   wherein the expelling of an amount of drug requires at least one user-actuated operation to be performed, and
   wherein the expelling of an amount of drug represents an administering event,
   the controller being adapted to:
   detect when a given user-actuated operation being part of the expelling of an amount of drug is performed,
   record detected operations as a function of time, and
   estimate, based on recorded operations, regimen time parameters for the detected operations, including:
   the periodicity, and
   a time or time window for each operation in the estimated period,
   thereby providing estimated time parameters for a medical regimen on which the detected operations are assumed to be based upon.

2. A drug delivery system as in claim 1, the system being configured to be set in a programming mode and a nonprogramming mode, wherein operations are detected and recorded when in the programming mode.

3. A drug delivery system as in claim 1, the system being configured to dynamically estimate time parameters incorporating most recent detected and recorded operations.

4. A drug delivery system as in claim 1, wherein the controller comprises information about a number of pre-defined regimens, the estimated parameters being matched to the best-fitting pre-defined regimen if possible for a given predefined confidence level.

5. A drug delivery system as in claim 1, wherein the system comprises:
   structure for receiving a drug reservoir,
   structure for detecting an identifier provided on a received drug reservoir,
   wherein the controller comprises information about at least two identifiers, each identifier being related with at least one predefined regimen, the estimated parameters being matched to the best-fitting predefined regimen if possible for a given predefined confidence level.

6. A drug delivery system as in claim 1, wherein the drug expelling structure comprises:
   setting structure allowing a user to set a dose amount to be expelled, and
   actuation structure for driving or releasing the drug expelling structure to expel the set dose.

7. A drug delivery system as in claim 6, wherein the controller is configured to detect the amount of drug expelled, the controller estimating for each action in an identified regimen an amount or a range of drug expelled.

8. A drug delivery system as in claim 6, wherein the system is configured to provide reminders to the user based on the estimated time parameters.

9. A drug delivery system as in claim 6, wherein the system is configured to provide warnings to the user based on the estimated time parameters and the actual use of the delivery system.

10. A drug delivery system as in claim 6, adapted to for a given time period calculate a compliance value based on calculated regimen time parameters and corresponding detected operations, the compliance value being indicative of the user's adherence to the regimen, wherein the compliance value is calculated for a user-selectable time period.

11. A drug delivery system as in claim 6, adapted to for a given time period calculate a compliance value based on the calculated regimen time parameters and corresponding detected operations, the compliance value being indicative of the user's adherence to the regimen, the drug delivery further being adapted to display compliance value information comprising icons selected in accordance with the degree of compliance.

12. A method adapted to estimate time parameters for a medical regimen comprising one or more administering events at a given time within a given period, comprising the steps:
   providing a system comprising:
   a controller,
   a drug reservoir or structure for receiving a drug reservoir,
   drug expelling structure for expelling an amount of drug from the reservoir,
   wherein the expelling of an amount of drug requires at least one user-actuated operation to be performed, and
   wherein the expelling of an amount of drug represents an administering event,
   detecting when a given user-actuated operation being part of the expelling of an amount of drug is performed,
   record detected operations as a function of time, and
   estimate, based on recorded operations, regimen time parameters for the detected operations, including:
   the periodicity, and
   a time or time window for each operation in the estimated period,
   thereby providing estimated time parameters for a medical regimen on which the detected operations are assumed to be based upon.

* * * * *